(12) United States Patent
McNeil et al.

(10) Patent No.: US 11,165,905 B2
(45) Date of Patent: Nov. 2, 2021

(54) AUTOMATIC IDENTIFICATION OF MEDICAL INFORMATION PERTINENT TO A NATURAL LANGUAGE CONVERSATION

(71) Applicant: International Business Machines Corporation, Armonk, NY (US)

(72) Inventors: Kristin E. McNeil, Charlotte, NC (US); Robert C. Sizemore, Fuquay-Varina, NC (US); David B. Werts, Charlotte, NC (US); Sterling R. Smith, Apex, NC (US); David G. Herbeck, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/545,585

(22) Filed: Aug. 20, 2019

(65) Prior Publication Data

US 2021/0058513 A1 Feb. 25, 2021

(51) Int. Cl.
*H04M 3/51* (2006.01)
*G16H 10/60* (2018.01)
*H04M 3/42* (2006.01)
*G06F 40/205* (2020.01)

(52) U.S. Cl.
CPC ......... *H04M 3/5116* (2013.01); *G06F 40/205* (2020.01); *G16H 10/60* (2018.01); *H04M 3/42034* (2013.01)

(58) Field of Classification Search
USPC ...................................................... 379/37–52
See application file for complete search history.

(56) References Cited

U.S. PATENT DOCUMENTS

| 10,044,857 | B2 * | 8/2018 | Philbin ................. H04M 3/46 |
| 2009/0119095 | A1 * | 5/2009 | Beggelman ............ G06F 40/30 704/9 |
| 2014/0122053 | A1 * | 5/2014 | Lotan .................... H04M 3/493 704/2 |

(Continued)

OTHER PUBLICATIONS

List of IBM Patents or Patent Applications Treated as Related, Feb. 5, 2020, 2 pages.

(Continued)

*Primary Examiner* — Maria El-Zoobi
(74) *Attorney, Agent, or Firm* — Francis Lammes; Stephen J. Walder, Jr.; William J. Stock

(57) ABSTRACT

A mechanism is provided for implementing an emergency response cognitive computing system. The emergency response cognitive computing system identifies a first party about which a communication is being performed between a caller and the emergency response system. The emergency response cognitive computing system generates, in real-time, a transcript of the communication as the communication is being conducted. The emergency response cognitive computing system performs natural language processing on the transcript of the communication to identify portions of content corresponding to medical concepts. The emergency response cognitive computing system processes patient information to identify elements of the patient information referencing concepts corresponding to medical concepts. The emergency response cognitive computing system outputs the elements of the patient information to a second party involved in the communication.

17 Claims, 4 Drawing Sheets

(56) References Cited

U.S. PATENT DOCUMENTS

| | | | |
|---|---|---|---|
| 2015/0164436 A1* | 6/2015 | Maron | A61B 5/7278 |
| | | | 340/540 |
| 2017/0060531 A1* | 3/2017 | Abbo | G10L 15/26 |
| 2020/0066414 A1* | 2/2020 | Neff | G16H 10/20 |
| 2020/0118164 A1* | 4/2020 | DeFrank | G06Q 30/0269 |

OTHER PUBLICATIONS

High, Rob, "The Era of Cognitive Systems: An Inside Look at IBM Watson and How it Works", IBM Corporation, Redbooks, Dec. 12, 2012, 16 pages.

Yuan, Michael J., "Watson and healthcare, How natural language processing and semantic search could revolutionize clinical decision support", IBM Corporation, IBM developerWorks, http://www.ibm.com/developerworks/industry/library/ind-watson/, Apr. 12, 2011, 14 pages.

* cited by examiner

AUTOMATIC IDENTIFICATION OF MEDICAL INFORMATION PERTINENT TO A NATURAL LANGUAGE CONVERSATION

BACKGROUND

The present application relates generally to an improved data processing apparatus and method and more specifically to mechanisms for automatic identification of medical information pertinent to a natural language conversation.

When a person contacts emergency services to indicate a medical emergency, information about the person with whom the emergency pertains is usually limited to answers provided to the questions asked by emergency personnel. These questions may include but are not limited to: an address of the emergency, the person's problem or the type of incident, approximate age of the person, whether the person is conscious, whether the person is breathing, or the like.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising a processor and a memory, the memory comprising instructions that are executed by the processor to configure the processor to implement an emergency response cognitive computing system. The illustrative embodiment identities, by the emergency response cognitive computing system, a first party about which a communication is being performed between a caller and the emergency response system. The illustrative embodiment generates, by the emergency response cognitive computing system, in real-time, a transcript of the communication as the communication is being conducted. The illustrative embodiment performs, by the emergency response cognitive computing system, natural language processing on the transcript of the communication to identify portions of content corresponding to medical concepts. The illustrative embodiment processes, by the emergency response cognitive computing system, patient information to identify elements of the patient information referencing concepts corresponding to medical concepts. The illustrative embodiment outputs, by the emergency response cognitive computing system, the elements of the patient information to a second party involved in the communication.

In other illustrative embodiments, a computer program product comprising a computer usable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
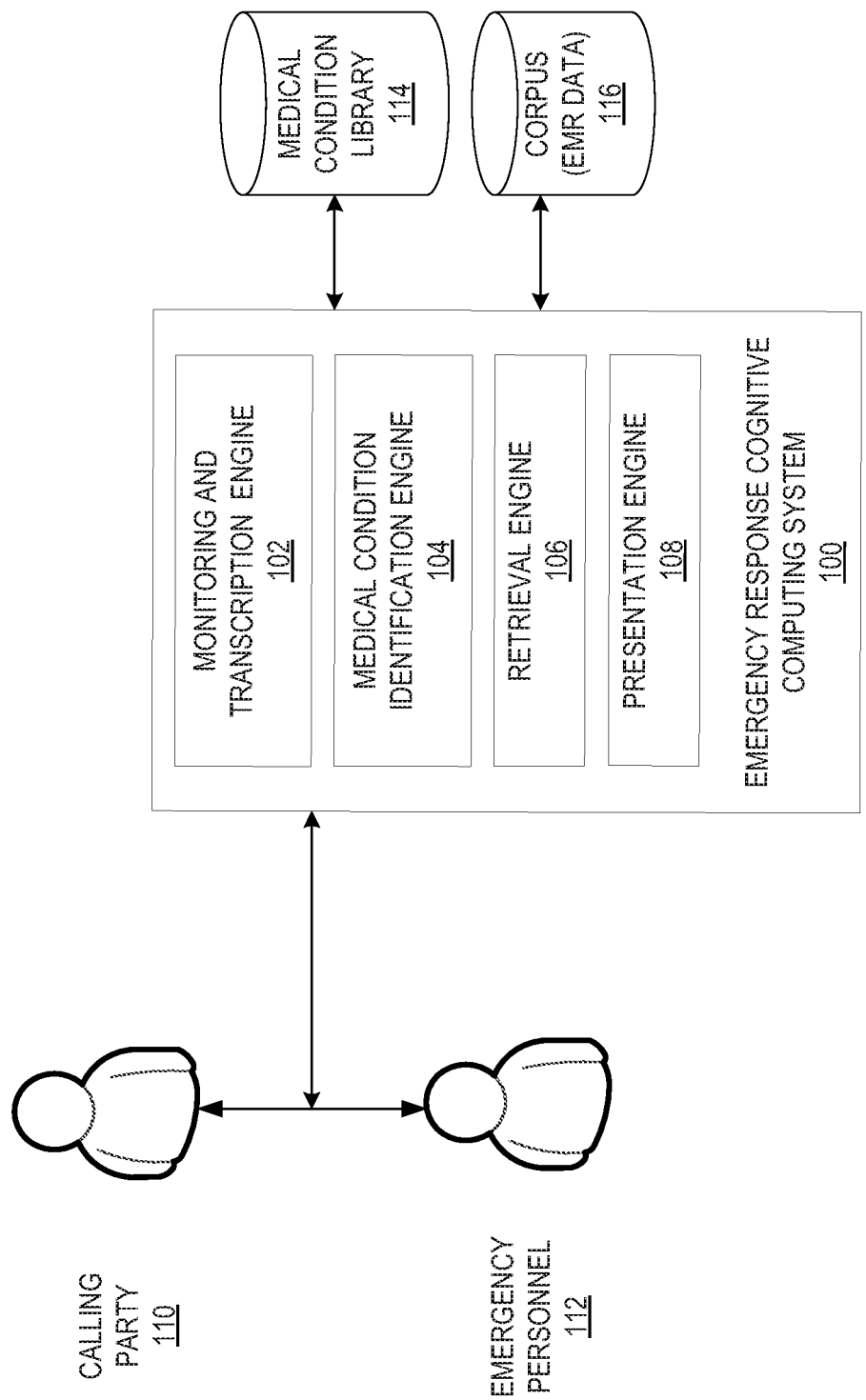
FIG. 1 is an example block diagram illustrating components of an emergency response cognitive computing system in accordance with one illustrative embodiment.

When a person contacts emergency services to indicate a medical emergency, often times the emergency personnel do not have access to medical information pertaining to the call. For example, if a person calls 911 and complains of chest pains, answers to questions such as: an address of the emergency, the person's problem or the type of incident, approximate age of the person, whether the person is conscious, whether the person is breathing, or the like, would not provide personal medical history about the person. Thus, the illustrative embodiments recognize that it would be beneficial to those responding to the call to know whether the particular person recently had heart surgery and was recently released from the hospital. In instances where persons are discussing a medical situation, such as when a person calls 911 or other emergency services, it would be helpful to be able to access personal medical information that is pertinent to the natural language conversation.

Therefore, the illustrative embodiments provide mechanisms for automatically identifying medical information pertinent to the natural language conversation and notifying medical personnel of the pertinent medical information. The illustrative embodiments provide a cognitive system that analyzes a transcription of the natural language conversation as it is occurring, such as by way of a chatbot type mechanism, and automatically retrieves pertinent medical information about one or more of the parties involved in the natural language conversation based on the medical concepts referenced in the natural language conversation for real-time presentation to one or more of the parties involved in the natural language conversation. Moreover, the pertinent medical information may also be forwarded to other parties which are associated with the natural language conversation being conducted. For example, appropriate notifications may be sent to care providers, such as emergency medical technicians (EMTs) on route, first responders, emergency room personnel waiting for the arrival of the patient, or the like. In some cases, the cognitive system may retrieve a person's electronic medical records (EMRs) and highlight pertinent portions for presentation to the appropriate personnel. Thus, the illustrative embodiments improve the ability of first responders to assist persons in emergency situations by automatically retrieving the most pertinent medical information needed by the first responders to understand an emergency situation and improve their ability to provide emergency care to one or more persons.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the illustrative embodiments of the present invention provides a methodology, apparatus, system and computer program product for automatically identifying medical information pertinent to a natural language conversation between emergency personnel and a caller and notifying medical personnel of the pertinent medical information. The following illustrates the operations of a cognitive system in analyzing a transcription of the natural language conversation between emergency personnel and one or more calling parties as it is occurring and automatically retrieving pertinent medical information about the one or more of the calling parties involved in the natural language conversation based on the medical concepts referenced in the natural language conversation. The cognitive system identifies the pertinent medical information and then presents the pertinent medical information in real-time to the emergency personnel involved in the natural language conversation. Moreover, the pertinent medical information may also be forwarded to other emergency personnel that are associated with the natural language conversation being conducted. For example, appropriate notifications may be sent to care providers, such as emergency medical technicians (EMTs) on route, first responders, emergency room personnel waiting for the arrival of the patient, or the like. In some cases, the cognitive system may retrieve a person's electronic medical records (EMRs) and highlight pertinent portions for presentation to the appropriate personnel.

FIG. 1 is an example block diagram illustrating components of a cognitive system for automatically identifying medical information of a patient pertinent to a natural language conversation between the patient and emergency personnel in accordance with one illustrative embodiment. As shown in FIG. 1, emergency response cognitive computing system 100 comprises monitoring and transcription engine 102, medical condition identification engine 104, retrieval engine 106, and presentation engine 108. Emergency response cognitive computing system 100 may be integrated with an emergency response system which may provide further information gathered by the emergency response system to assist in identifying the additional medical information to be retrieved and presented.

In operation, as a real-time communication is conducted between calling party 110 and emergency personnel 112. For example, emergency response cognitive computing system 100 may be integrated in, or otherwise operate in conjunction with, a 911 response computing system or the like, which may itself collect information about persons contacting the emergency service, e.g., caller identification information, information about callers entered manually by emergency personnel 112, such as an address of the emergency, a name of the patient (which may not be the same as calling party 110), a medical issue being experienced by the patient, approximate age of the patient, whether the patient is conscious, whether the patient is breathing, and the like. Emergency personnel 112 may enter this information into an appropriate interface of the 911 computer system and thus, emergency response cognitive computing system 100. Alternatively, an identity of the person or persons that is the subject of the call may be automatically determined from identifiers automatically identified by the computer system itself, e.g., automated caller ID information.

Thus, monitoring and transcription engine 102 monitors the real-time communication between calling party 110 and emergency personnel 112 as well as any data automatically identified. For the entire real-time communication, monitoring and transcription engine 102 transcribes the real-time communication as well as any automatically identified data into a real-time transcription file. As monitoring and transcription engine 102 is transcribing the real-time communication into the real-time transcription file, medical condition identification engine 104 performs natural language processing on the text of the real-time transcription file to identify terms/phrases indicative of medical conditions identified in the real-time transcription file for which user specific medical information is desirable to provide a complete understanding of the context of the real-time communication.

In order to identify terms/phrases indicative of medical conditions identified in the real-time transcription file for which user specific medical information is desirable to provide a complete understanding of the context of the real-time communication, medical condition identification engine 104 compares each identified term or set of terms (i.e. a phrase) to one or more terms or set of terms in medical condition library 114, which may be a medical condition library such as the Unified Medical Language System (UMLS) that is a set of files and software that brings together many health and biomedical vocabularies and standards to enable interoperability between computer systems. For each medical condition identified in the real-time transcription file, retrieval engine 106 searches for associated medical information from electronic medical records (EMRs) 116 associated with the patient identified by calling party 110. Thus, retrieval engine 106 identifies portions of the patient's information that is most relevant to the issues being discussed during the real-time communication through the performance of emergency response cognitive computing system 100. For example, if calling party 110 identifies that the patient is complaining of chest pains, then this may be used to search patient EMRs 116 to determine if the patient has had any medical conditions, procedures, symptoms, or the like, that are related to chest pains. Thus, if the patient has recently had a heart attack, then this information may be identified in patient EMRs.

Responsive to retrieval engine 106 identifying any associated medical information from electronic medical records (EMRs) 116 associated with the patient, presentation engine 108 highlights or otherwise presents the associated medical information to one or more emergency personnel, such as emergency personnel 112 and/or other emergency personnel that are designated as authorized recipients of such information, which may be determined dynamically at the time of the conversation, e.g., EMTs assigned to respond, doctors, nurses, or other medical personnel have been assigned to the case, or the like, which may include emergency room doctors, nurses, or other medical personnel, the patient's personal doctor, or the like. The highlighting or otherwise presenting the associated medical information to one or more emergency personnel may involve sending such information from the emergency system to other computing systems or communication systems remotely located from the emergency system.

Figure 2:
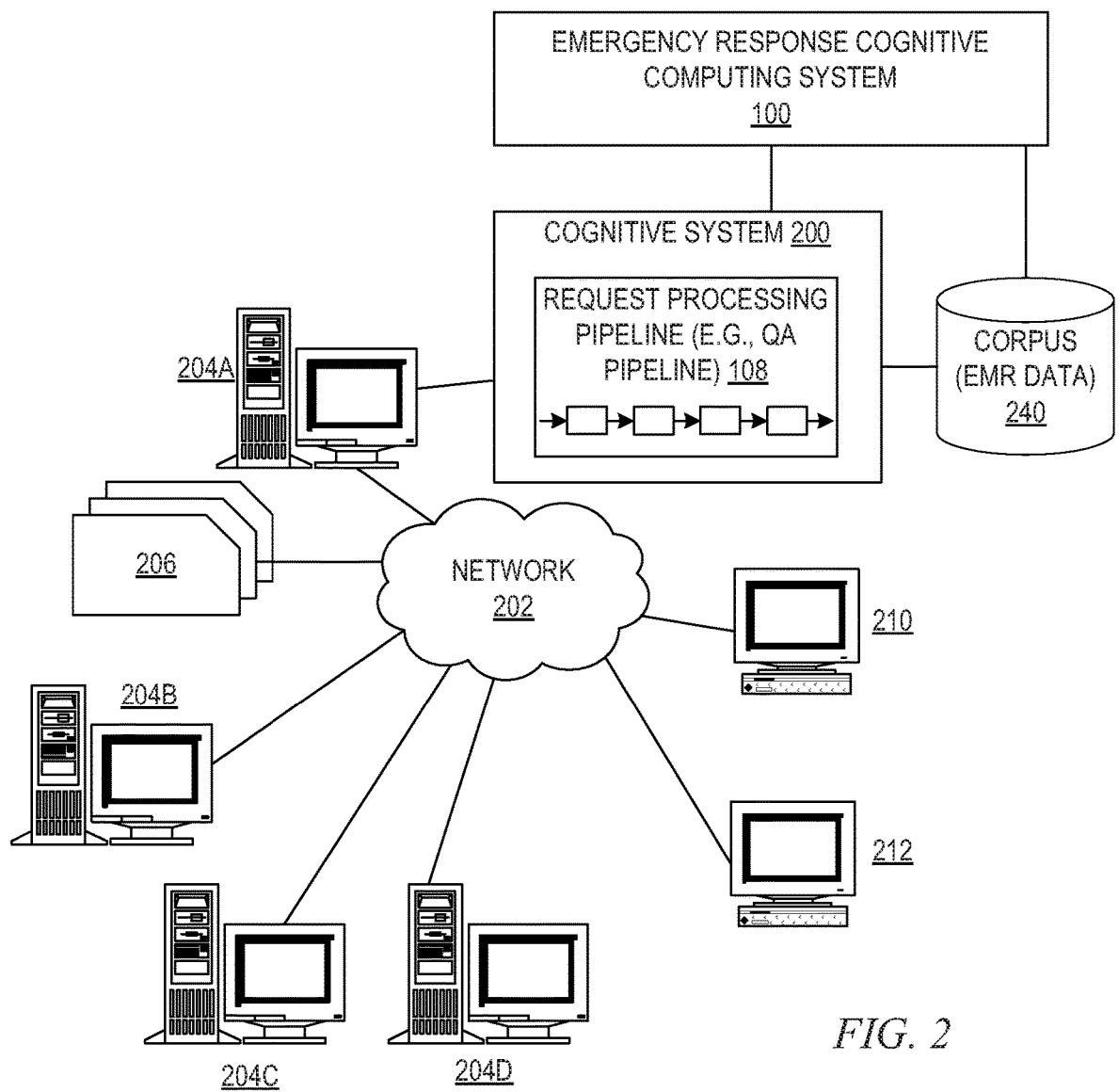
FIG. 2 depicts a schematic diagram of one illustrative embodiment of a cognitive healthcare system in a computer network.
Figure 3:
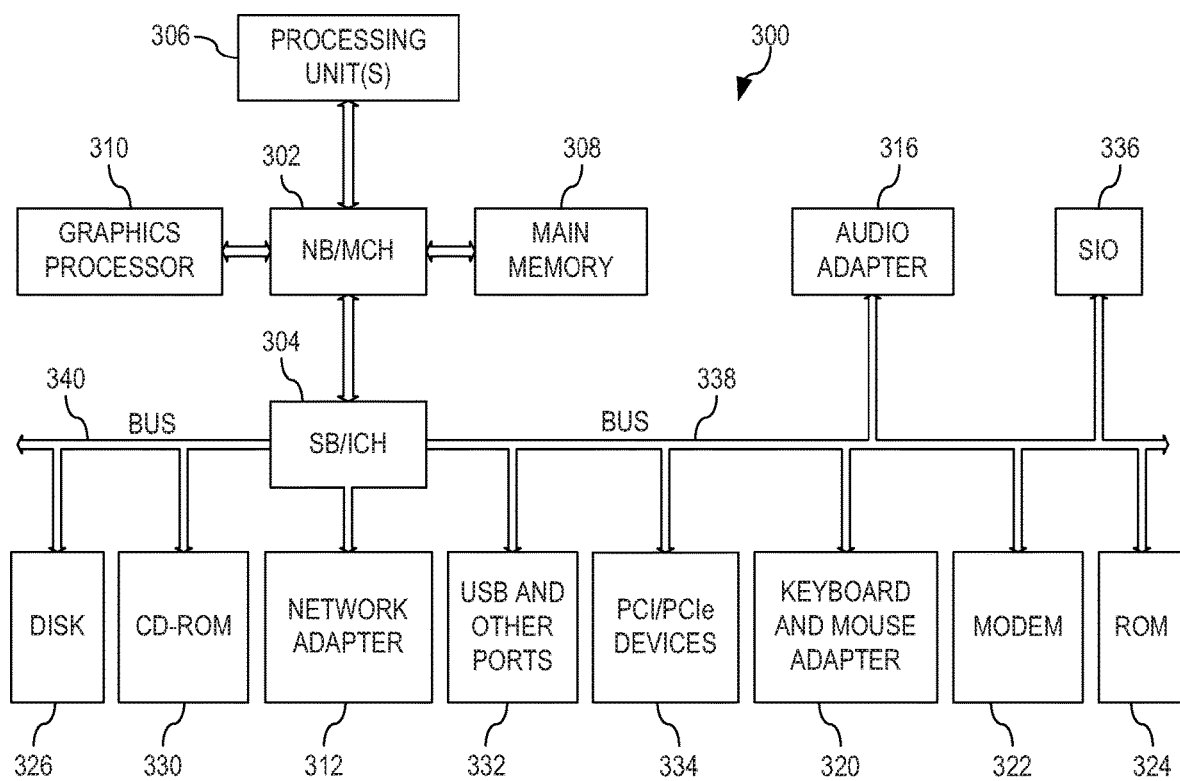
FIG. 3 is a block diagram of an example data processing system in which aspects of the illustrative embodiments are implemented.

It is clear from the above, that the illustrative embodiments may be utilized in many different types of data processing environments. In order to provide a context for the description of the specific elements and functionality of the illustrative embodiments, FIGS. 2-3 are provided hereafter as example environments in which aspects of the illustrative embodiments may be implemented. It should be appreciated that FIGS. 2-3 are only examples and are not intended to assert or imply any limitation with regard to the environments in which aspects or embodiments of the present invention may be implemented. Many modifications to the depicted environments may be made without departing from the spirit and scope of the present invention.

FIGS. 2-3 are directed to describing an example cognitive system for presenting patient associated medical information to be utilized by emergency personnel responding to a medical issue of the patient that implements a request processing pipeline, request processing methodology, and request processing computer program product with which the mechanisms of the illustrative embodiments are implemented. These requests may be provided as structure request messages, unstructured request messages or any other suitable format for requesting an operation to be performed by the cognitive system. As described in more detail hereafter, the particular application that is implemented in the cognitive system of the present invention is an application for presenting contextually relevant patient data in relation to other patients to a medical professional in a graphical user interface.

It should be appreciated that the cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests, depending on the desired implementation. For example, in some cases, a first request processing pipeline may be trained to operate on input requests directed to identifying a medical condition based on transcripts of a real-time communication between a calling party and emergency personnel. In other cases, for example, the request processing pipelines may be configured to identify associated medical information front a patient's electronic medical records based on an identified medical condition from a real-time communication between a calling party and emergency personnel.

Moreover, each request processing pipeline may have its own associated corpus or corpora that they ingest and operate on, e.g., one corpus for medical condition documents and another corpus for electronic medical record documents in the above examples. In some cases, the request processing pipelines may each operate on the same domain of requests but may have different configurations, e.g., different annotators or differently trained annotators, such that different analysis and potential responses are generated. The cognitive system may provide additional logic for routing requests to the appropriate request processing pipeline, such as based on a determined domain of the input request, combining and evaluating final results generated by the processing performed by multiple request processing pipelines, and other control and interaction logic that facilitates the utilization of multiple request processing pipelines.

It should be appreciated that while the present invention will be described in the context of the cognitive system implementing one or more request processing pipelines that operate on a request, the illustrative embodiments are not limited to such. Rather, the mechanisms of the illustrative embodiments may operate on requests that are posed as "questions" or formatted as requests for the cognitive system to perform cognitive operations on a specified set of input data using the associated corpus or corpora and the specific configuration information used to configure the cognitive system.

As will be discussed in greater detail hereafter, the illustrative embodiments may be integrated in, augment, and extend the functionality of the request processing pipeline with regard to identifying issues associated with the medical treatments for the medical condition of the patent and presenting a corresponding alerts or notifications. For example, identifying one or more medical conditions of the patient that include a medication that the patient experienced an adverse reaction to, a medication that has caused unwanted side effects, a medication that has not helped control the patient's medical condition, or the like.

It should be appreciated that the mechanisms described in FIGS. 2-3 are only examples and are not intended to state or imply any limitation with regard to the type of cognitive system mechanisms with which the illustrative embodiments are implemented. Many modifications to the example cognitive system shown in FIGS. 2-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding,
Ingest and process vast amounts of structured and unstructured data,
Generate and evaluate hypothesis,
Weigh and evaluate responses that are based only on relevant evidence,
Provide situation-specific advice, insights, and guidance,
Improve knowledge and learn with each iteration and interaction through machine learning processes,
Enable decision making at the point of impact (contextual guidance),
Scale in proportion to the task,
Extend and magnify human expertise and cognition,
Identify resonating, human-like attributes and traits from natural language,
Deduce various language specific or agnostic attributes from natural language,
High degree of relevant recollection from data points (images, text, voice) (memorization and recall),
Predict and sense with situational awareness that mimic human cognition based on experiences, or
Answer questions based on natural language and specific evidence.

In one aspect, cognitive systems provide mechanisms for responding to requests posed to these cognitive systems using a request processing pipeline and/or process requests which may or may not be posed as natural language requests. The requests processing pipeline is an artificial intelligence application executing on data processing hardware that responds to requests pertaining to a given subject-matter domain presented in natural language. The request processing pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the request processing pipeline. The document may include any file, text, article, or source of data for use in the requests processing system. For example, a request processing pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input requests to cognitive system which implements the request processing pipeline. The request processing pipeline then responds to the requests using the content in the corpus of data by evaluating documents, sections of documents, portions of data in the corpus, or the like. When a process evaluates a given section of a document for semantic content, the process can use a variety of conventions to query such document from the request processing pipeline, e.g., sending the query to the request processing pipeline as a well-formed requests which is then interpreted by the request processing pipeline and a response is provided containing one or more responses to the request. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the request processing pipeline receives a request, parses the request to extract the major features of the request, uses the extracted features to formulate queries, and then applies those queries to the corpus of data. Based on the application of the queries to the corpus of data, the request processing pipeline generates a set of responses to the request, by looking across the corpus of data for portions of the corpus of data that have some potential for containing a valuable response to the request. The request processing pipeline then performs deep analysis on the language of the request and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the request and the found portions of the corpus of data. Other reasoning algorithms may look at temporal or spatial features in the language, while others may evaluate the source of the portion of the corpus of data and evaluate its veracity.

As mentioned above, request processing pipeline mechanisms operate by accessing information from a corpus of data or information (also referred to as a corpus of content), analyzing it, and then generating answer results based on the analysis of this data. Accessing information from a corpus of data typically includes: a database query that answers requests about what is in a collection of structured records, and a search that delivers a collection of document links in response to a query against a collection of unstructured data (text, markup language, etc.). Conventional request processing systems are capable of generating answers based on the corpus of data and the input request, verifying answers to a collection of request for the corpus of data, correcting errors in digital text using a corpus of data, and selecting responses to requests from a pool of potential answers, i.e. candidate answers.

FIG. 2 depicts a schematic diagram of one illustrative embodiment of a cognitive system 200 implementing a request processing pipeline 208, which in some embodiments may be a request processing pipeline, in a computer network 202. For purposes of the present description, it will be assumed that the request processing pipeline 208 is implemented as a request processing pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 200 is implemented on one or more computing devices 204A-D (comprising one or more processors and one or more memories, and potentially any other computing device elements generally known in the art including buses, storage devices, communication interfaces, and the like) connected to the computer network 202. For purposes of illustration only, FIG. 2 depicts the cognitive system 200 being implemented on computing device 204A only, but as noted above the cognitive system 200 may be distributed across multiple computing devices, such as a plurality of computing devices 204A-D. The network 202 includes multiple computing devices 204A-D, which may operate as server computing devices, and 210-212 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 200 and network 202 enables question processing and answer generation (QA) functionality for one or more cognitive system users via their respective computing devices 210-212. In other embodiments, the cognitive system 200 and network 202 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 200 may be used with components, systems, sub-systems, and/or devices other than those that are depicted herein.

The cognitive system 200 is configured to implement a request processing pipeline 208 that receive inputs from various sources. The requests may be posed in the form of a natural language question, natural language request for information, natural language request for the performance of a cognitive operation, or the like. For example, the cognitive system 200 receives input from the network 202, a corpus or corpora of electronic documents 206, cognitive system users, and/or other data and other possible sources of input. In one embodiment, some or all of the inputs to the cognitive system 200 are routed through the network 202. The various computing devices 204A-D on the network 202 include access points for content creators and cognitive system users. Some of the computing devices 204A-D includes devices for a database storing the corpus or corpora of data 206 (which is shown as a separate entity in FIG. 2 for illustrative purposes only). Portions of the corpus or corpora of data 206 may also be provided on one or more other network attached storage devices, in one or more databases, or other computing devices not explicitly shown in FIG. 2. The network 202 includes local network connections and remote connections in various embodiments, such that the cognitive system 200 may operate in environments of any size, including local and global, e.g., the Internet.

In one embodiment, the content creator creates content in a document of the corpus or corpora of data 206 for use as part of a corpus of data with the cognitive system 200. The document includes any file, text, article, or source of data for use in the cognitive system 200. Cognitive system users access the cognitive system 200 via a network connection or an Internet connection to the network 202, and requests to the cognitive system 200 that are responded to/processed based on the content in the corpus or corpora of data 206. In one embodiment, the requests are formed using natural language. The cognitive system 200 parses and interprets the request via a pipeline 208, and provides a response to the cognitive system user, e.g., cognitive system user 210, containing one or more responses to the request posed, response to the request, results of processing the request, or the like. In some embodiments, the cognitive system 200 provides a response to users in a ranked list of candidate answers/responses while in other illustrative embodiments, the cognitive system 200 provides a single final response or a combination of a response and ranked listing of other candidate responses.

The cognitive system 200 implements the pipeline 208 which comprises a plurality of stages for processing a request based on information obtained from the corpus or corpora of data 206. The pipeline 208 generates responses for the request based on the processing of the request and the corpus or corpora of data 206.

In some illustrative embodiments, the cognitive system 200 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives a request which it then parses to extract the major features of the request, which in turn are then used to formulate queries that are applied to the corpus or corpora of data 206. Based on the application of the queries to the corpus or corpora of data 206, a set of hypotheses, or candidate responses to the request, are generated by looking across the corpus or corpora of data 206 for portions of the corpus or corpora of data 206 (hereafter referred to simply as the corpus 206) that have some potential for containing a valuable response to the response. The pipeline 208 of the IBM Watson™ cognitive system then performs deep analysis on the language of the request and the language used in each of the portions of the corpus 206 found during the application of the queries using a variety of reasoning algorithms.

The scores obtained from the various reasoning algorithms are then weighted against a statistical model that summarizes a level of confidence that the pipeline 208 of the IBM Watson™ cognitive system 200, in this example, has regarding the evidence that the potential candidate answer is interred by the request. This process is repeated for each of the candidate answers to generate a ranked listing of candidate answers which may then be presented to the user that submitted the request, e.g., a user of client computing device 210, or from which a final response is selected and presented to the user. More information about the pipeline 208 of the IBM Watson™ cognitive system 200 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 200 from a client device may be posed in the form of a natural language request, the illustrative embodiments are not limited to such. Rather, the request may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result. In particular, the mechanisms of the healthcare based cognitive system may process drug-adverse events or adverse drug reaction pairings when performing the healthcare oriented cognitive system result, e.g., a diagnosis or treatment recommendation.

In the context of the present invention, cognitive system 200 may provide a cognitive functionality for assisting with healthcare based operations. For example, depending upon the particular implementation, the healthcare based operations may comprise patient diagnostics, medical treatment recommendation systems, personal patient care plan generation and monitoring, patient electronic medical record (EMR) evaluation for various purposes, such as for identifying patients that are suitable for a medical trial or a particular type of medical treatment, or the like. Thus, the cognitive system 200 may be a healthcare cognitive system 200 that operates in the medical or healthcare type domains and which may process requests for such healthcare operations via the request processing pipeline 208 input as either structured or unstructured requests, natural language input requests, or the like. In one illustrative embodiment, the cognitive system 200 is an emergency response cognitive computing system that presents associated patient medical information to be utilized by emergency personnel responding to a medical issue of the patient.

As shown in FIG. 2, the cognitive system 200 is further augmented, in accordance with the mechanisms of the illustrative embodiments, to include logic implemented in specialized hardware, software executed on hardware, or any combination of specialized hardware and software executed on hardware, for implementing an emergency response cognitive computing system 100. As described previously, the emergency response cognitive computing system 100 performs an identification of medical conditions from a transcription of a real-time communication between a calling party and emergency personnel and presents associated patient medical information to be utilized by emergency personnel responding to a medical issue of a patient.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 3 is provided as an example of one type of data processing system in which aspects of the present invention may be implemented. Many other types of data processing systems may be likewise configured to specifically implement the mechanisms of the illustrative embodiments.

FIG. 3 is a block diagram of an example data processing system in which aspects of the illustrative embodiments are implemented. Data processing system 300 is an example of a computer, such as server 204A or client 210 in FIG. 2, in which computer usable code or instructions implementing the processes for illustrative embodiments of the present invention are located. In one illustrative embodiment, FIG. 3 represents a server computing device, such as a server 204, which, which implements a cognitive system 200 and QA system pipeline 208 augmented to include the additional mechanisms of the illustrative embodiments described hereafter.

In the depicted example, data processing system 300 employs a hub architecture including North Bridge and Memory Controller Hub (NB/MCH) 302 and South Bridge and Input/Output (I/O) Controller Hub (SB/ICH) 304. Processing unit 306, main memory 308, and graphics processor 310 are connected to NB/MCH 302. Graphics processor 310 is connected to NB/MCH 302 through an accelerated graphics port (AGP).

In the depicted example, local area network (LAN) adapter 312 connects to SB/ICH 304. Audio adapter 316, keyboard and mouse adapter 320, modem 322, read only memory (ROM) 324, hard disk drive (HDD) 326, CD-ROM drive 330, universal serial bus (USB) ports and other communication ports 332, and PCI/PCIe devices 334 connect to SB/ICH 304 through bus 338 and bus 340. PCI/PCIe devices may include, for example, Ethernet adapters, add-in cards, and PC cards for notebook computers. PCI uses a card bus controller, while Pete does not. ROM 324 may be, for example, a flash basic input/output system (BIOS).

HDD 326 and CD-ROM drive 330 connect to SB/ICH 304 through bus 340, HDD 326 and CD-ROM drive 330 may use, for example, an integrated drive electronics (IDE) or serial advanced technology attachment (SATA) interface. Super I/O (SIO) device 336 is connected to SB/ICH 304.

An operating system runs on processing unit 306. The operating system coordinates and provides control of various components within the data processing system 300 in FIG. 3. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 300.

As a server, data processing system 300 may be, for example, an IBM® eServer™ System p® computer system, running the Advanced Interactive Executive (AIX®) operating system or the LINUX® operating system. Data processing system 300 may be a symmetric multiprocessor (SMP) system including a plurality of processors in processing unit 306. Alternatively, a single processor system may be employed.

Instructions for the operating system, the object-oriented programming system, and applications or programs are located on storage devices, such as HDD 326, and are loaded into main memory 308 for execution by processing unit 306. The processes for illustrative embodiments of the present invention are performed by processing unit 306 using computer usable program code, which is located in a memory such as, for example, main memory 308, ROM 324, or in one or more peripheral devices 326 and 330, for example.

A bus system, such as bus 338 or bus 340 as shown in FIG. 3, is comprised of one or more buses. Of course, the bus system may be implemented using any type of communication fabric or architecture that provides for a transfer of data between different components or devices attached to the fabric or architecture. A communication unit, such as modem 322 or network adapter 312 of FIG. 3, includes one or more devices used to transmit and receive data. A memory may be, for example, main memory 308, ROM 324, or a cache such as found in NB/MCH 302 in FIG. 3.

Those of ordinary skill in the art will appreciate that the hardware depicted in FIGS. 2 and 3 may vary depending on the implementation. Other internal hardware or peripheral devices, such as flash memory, equivalent non-volatile memory, or optical disk drives and the like, may be used in addition to or in place of the hardware depicted in FIGS. 2 and 3. Also, the processes of the illustrative embodiments may be applied to a multiprocessor data processing system, other than the SMP system mentioned previously, without departing from the spirit and scope of the present invention.

Moreover, the data processing system 300 may take the form of any of a number of different data processing systems including client computing devices, server computing devices, a tablet computer, laptop computer, telephone or other communication device, a personal digital assistant (PDA), or the like. In some illustrative examples, data processing system 300 may be a portable computing device that is configured with flash memory to provide non-volatile memory for storing operating system files and/or user-generated data, for example. Essentially, data processing system 300 may be any known or later developed data processing system without architectural limitation.

Figure 4:
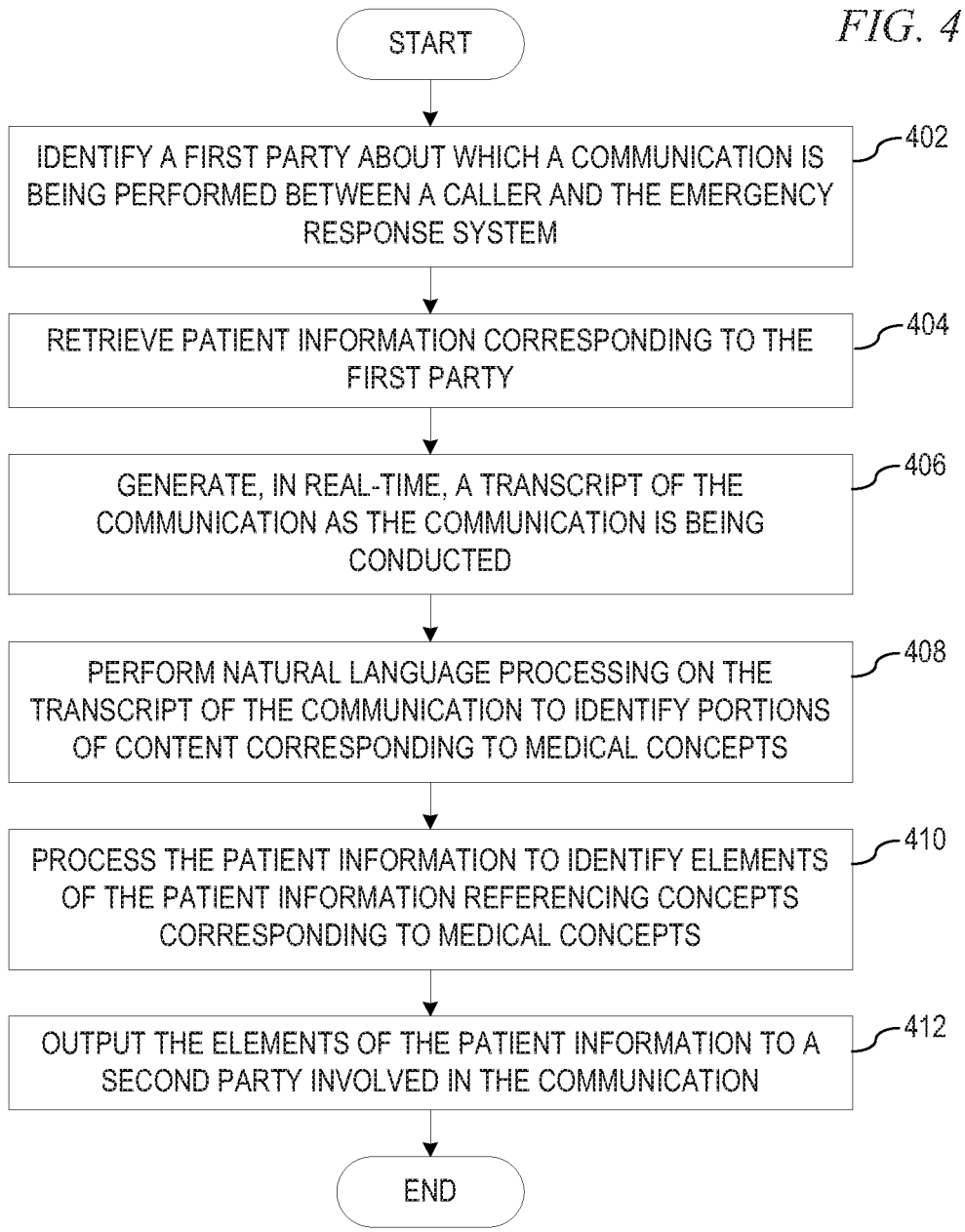
FIG. 4 is a flowchart outlining example operations performed by an emergency response cognitive computing system in automatically identifying medical information pertinent to a natural language conversation and notifying medical personnel in accordance with one illustrative embodiment.

FIG. 4 is a flowchart outlining example operations performed by an emergency response cognitive computing system in automatically identifying medical information pertinent to a natural language conversation and notifying medical personnel in accordance with one illustrative embodiment. As the exemplary operation begins, the emergency response cognitive computing system identifies a first party about which a communication is being performed between a caller and the emergency response system (step 402). The emergency response cognitive computing system retrieves patient information corresponding to the first party (step 404). The emergency response cognitive computing system generates, in real-time, a transcript of the communication as the communication is being conducted (step 406). The emergency response cognitive computing system performs natural language processing on the transcript of the communication to identify portions of content corresponding to medical concepts (step 408). The emergency response cognitive computing system processes the patient information to identify elements of the patient information referencing concepts corresponding to medical concepts (step 410). The emergency response cognitive computing system then outputs the elements of the patient information to a second party involved in the communication (step 412), with the operation ending thereafter.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, wherein the at least one memory comprises instructions that are executed by the at least one processor to configure the at least one processor to implement an emergency response cognitive computing system, the method comprising:

identifying, by the emergency response cognitive computing system, a first party about which a communication is being performed between a caller and the emergency response system;

generating, by the emergency response cognitive computing system, in real-time, a transcript of the communication as the communication is being conducted;

performing, by the emergency response cognitive computing system, natural language processing on the transcript of the communication to identify portions of content corresponding to medical concepts, wherein the portions of content corresponding to the medical concepts from the transcript of the communication are identified by comparing each term or each set of terms in the transcript of the communication to one or more terms or set of terms in a medical condition library;

processing, by the emergency response cognitive computing system, patient information to identify elements of the patient information referencing concepts corresponding to the medical concepts; and outputting, by the emergency response cognitive computing system, the elements of the patient information to a second party involved in the communication.

2. The method of claim 1, wherein the first party is identified based on information entered into the emergency response system based on information provided by the caller.

3. The method of claim 1, wherein the first party is identified based on automated caller identification.

4. The method of claim 1, wherein the emergency response cognitive computing system is integrated into the emergency response system.

5. The method of claim 1, wherein the patient information is electronic medical records of the patient.

6. The method of claim 1, wherein the second party is one or more of an emergency personnel on the other end of the communication, an emergency medical technician assigned to respond to the first party, a medical professional assigned to treat the patient once transported to an medical facility, or a personal doctor of the first party.

7. A computer program product comprising a non-transitory computer readable storage medium having a computer readable program stored therein, wherein the computer readable program, when executed on a data processing system, causes the data processing system to implement an emergency response cognitive computing system, and further causes the data processing system to:

identify, by the emergency response cognitive computing system, a first party about which a communication is being performed between a caller and the emergency response system;

generate, by the emergency response cognitive computing system, in real-time, a transcript of the communication as the communication is being conducted;

perform, by the emergency response cognitive computing system, natural language processing on the transcript of the communication to identify portions of content corresponding to medical concepts, wherein the portions of content corresponding to the medical concepts from the transcript of the communication are identified by comparing each term or each set of terms in the transcript of the communication to one or more terms or set of terms in a medical condition library;

process, by the emergency response cognitive computing system, patient information to identify elements of the patient information referencing concepts corresponding to the medical concepts; and output, by the emergency response cognitive computing system, the elements of the patient information to a second party involved in the communication.

8. The computer program product of claim 7, wherein the first party is identified based on information entered into the emergency response system based on information provided by the caller.

9. The computer program product of claim 7, wherein the first party is identified based on automated caller identification.

10. The computer program product of claim 7, wherein the emergency response cognitive computing system is integrated into the emergency response system.

11. The computer program product of claim 7, wherein the patient information is electronic medical records of the patient.

12. The computer program product of claim 7, wherein the second party is one or more of an emergency personnel on the other end of the communication, an emergency medical technician assigned to respond to the first party, a medical professional assigned to treat the patient once transported to an medical facility, or a personal doctor of the first party.

13. A data processing system comprising:
at least one processor; and
at least one memory coupled to the at least one processor, wherein the at least one memory comprises instructions which, when executed by the at least one processor, cause the at least one processor to implement an emergency response cognitive computing system, and further cause the at least one processor to:

identify, by the emergency response cognitive computing system, a first party about which a communication is being performed between a caller and the emergency response system;

generate, by the emergency response cognitive computing system, in real-time, a transcript of the communication as the communication is being conducted;

perform, by the emergency response cognitive computing system, natural language processing on the transcript of the communication to identify portions of content corresponding to medical concepts, wherein the portions of content corresponding to the medical concepts from the transcript of the communication are identified by comparing each term or each set of terms in the transcript of the communication to one or more terms or set of terms in a medical condition library;

process, by the emergency response cognitive computing system, patient information to identify elements of the patient information referencing concepts corresponding to the medical concepts; and output, by the emergency response cognitive computing system, the elements of the patient information to a second party involved in the communication.

14. The data processing system of claim 13, wherein the first party is identified based on information entered into the emergency response system based on information provided by the caller.

15. The data processing system of claim 13, wherein the first party is identified based on automated caller identification.

16. The data processing system of claim 13, wherein the patient information is electronic medical records of the patient.

17. The data processing system of claim 13, wherein the second party is one or more of an emergency personnel on the other end of the communication, an emergency medical technician assigned to respond to the first party, a medical professional assigned to treat the patient once transported to an medical facility, or a personal doctor of the first party.

\* \* \* \* \*